United States Patent [19]

Newman

[11] 4,173,225
[45] Nov. 6, 1979

[54] ADJUSTABLE STOP FOR DISPENSING SYRINGE

[75] Inventor: Howard F. Newman, Los Angeles, Calif.

[73] Assignee: American Hospital Supply Corporation, Evanston, Ill.

[21] Appl. No.: 836,995

[22] Filed: Sep. 27, 1977

[51] Int. Cl.² ............................................. A61M 5/00
[52] U.S. Cl. ................................. 128/218 C; 128/234
[58] Field of Search ............... 128/215, 218 R, 218 C, 128/218 F, 220, 221, 234

[56] References Cited

U.S. PATENT DOCUMENTS

| 2,863,452 | 12/1958 | Ogle | 128/218 |
| 3,783,876 | 1/1974 | Dye | 128/347 |
| 3,831,602 | 8/1974 | Broadwin | 128/218 F |
| 3,965,945 | 6/1976 | Ross | 141/27 |

FOREIGN PATENT DOCUMENTS 2362638  10/1976  France ................................ 128/218 C Primary Examiner—John D. Yasko
Attorney, Agent, or Firm—Larry N. Barger

[57] ABSTRACT

A dispensing syringe that has a slidable dose control rod with an adjustable cam locking stop on the rod.

6 Claims, 4 Drawing Figures

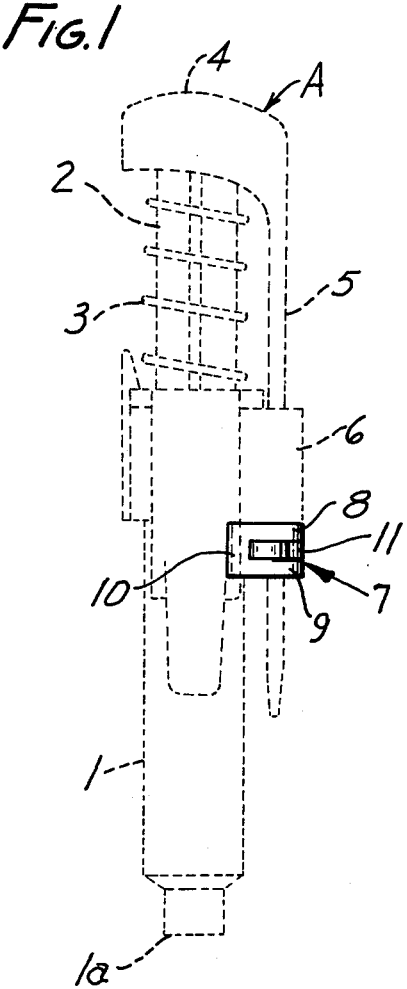
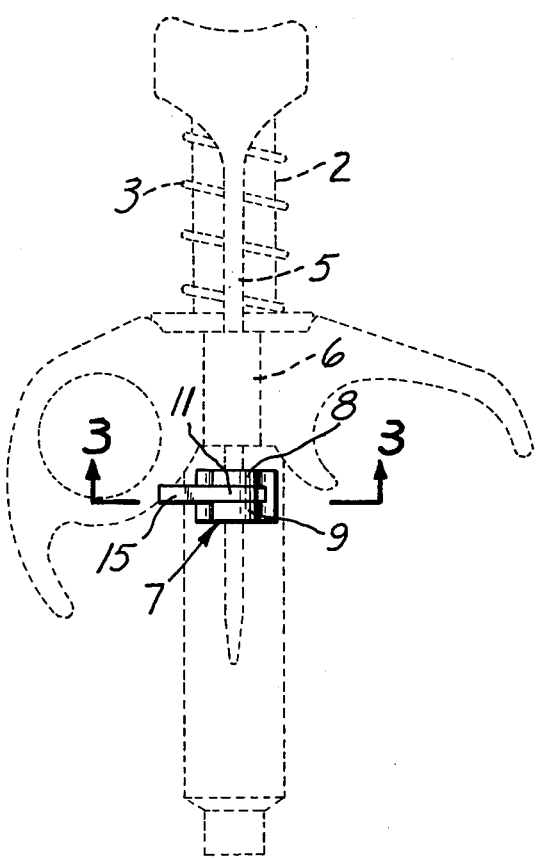
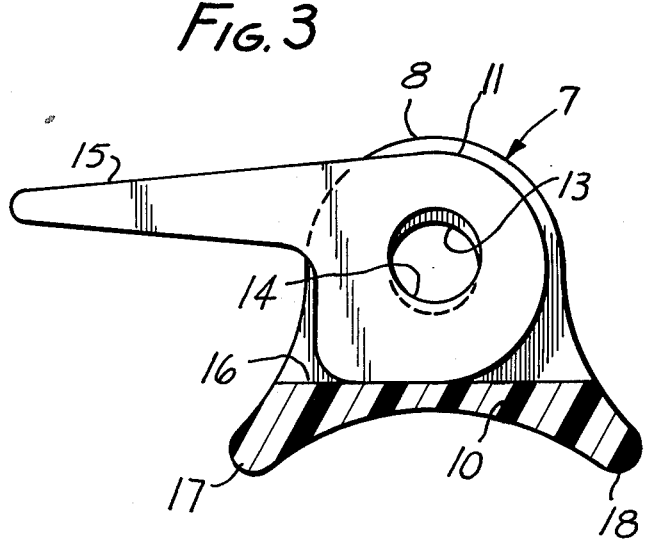
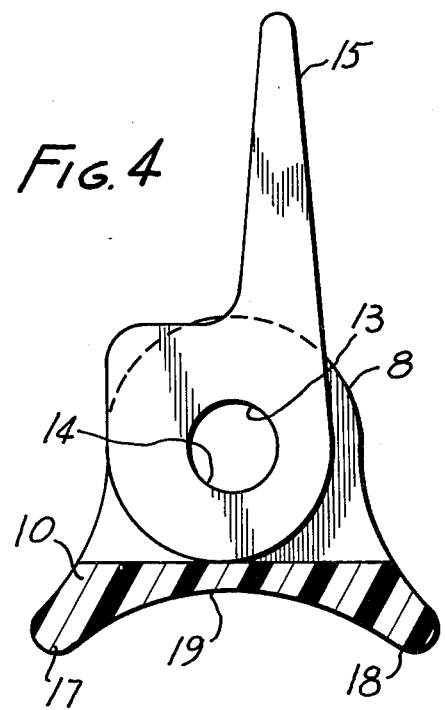

ADJUSTABLE STOP FOR DISPENSING SYRINGE

BACKGROUND OF THE INVENTION

A dispensing syringe with an adjustable dose setting mechanism is described in a co-pending application entitled Syringe Pumping Handle Grip and Method of Assembling Same, of Bloom et al, Ser. No. 747,417, Filed Dec. 6, 1976, now U.S. Pat. No. 4,098,276. That application describes a coil spring stop that is adjustably mounted on a rod-like dose control rod.

It has been found that under long continuous use the coil spring stop of the above application is sufficiently easy to manually adjust, but does tend to creep from its initial setting with long continued use of the dispensing syringe. Thus, it may be necessary to periodically re-check the setting and correct any deviation slippage of the stop on its supporting rod.

SUMMARY OF THE INVENTION

This invention is an improvement on a stop mechanism for a dispensing syringe that is very easy to adjust, but still gives very tight noncreeping gripping attachment to a rod-like member of a dispensing syringe. The stop includes a pair of members with openings that receive the rod-like member, and a cam on one of the members engages the other member to cause the holes to misalign and thereby firmly gripping the rod-like member. A form of the invention is shown that includes a U-shaped base with a pair of arms having openings through which the rod-like member extends. A clamping member with an opening for the rod fits between the arms of the base and has a cam structure for misaligning openings in the base and clamping structure. Preferably the base has a recess for slidingly receiving a portion of a cylindrical syringe barrel to keep the base from rotating on the rod-like member during adjustment.

THE DRAWINGS

FIG. 1 is a side elevational view of a dispensing syringe with the adjustable stop abutting a portion of the syringe;

FIG. 2 is a front elevational view of the syringe of FIG. 1, but with the syringe plunger slightly depressed and the adjustable stop moved from the abutting configuration of FIG. 1;

FIG. 3 is an enlarged sectional view taken along line 3—3 of FIG. 2 showing the adjustable stop in clamped position; and FIG. 4 is an enlarged sectional view similar to FIG. 3, but showing the adjustable stop in unclamped position.

DETAILED DESCRIPTION

In FIG. 1 a syringe barrel 1 is shown with a longitudinally slidable plunger 2 that is urged toward a fully retracted position by compression coil spring 3. Limiting the position of the retracted plunger 2 is a dose control device 3 that includes a cap 4 fitting over the plunger 2 and a metering rod 5. Metering rod 5 is longitudinally slidable within an opening in a handle portion 6 that fits on syringe barrel 1. The details of the syringe handle 6, and metering rod 5 are shown in the co-pending application by Bloom et al previously mentioned. It is well understood that a forward tip 7 of the syringe barrel 1 can connect to a dispensing tube, needle, etc.

Fitting on metering rod 5 is a cam locking step mechanism that includes a U-shaped base 7 with a pair of arms 8 and 9. Arms 8 and 9 have aligned openings through which metering rod 5 extends. The U-shaped member also has a floor section 10 which can slide along the syringe barrel 1 as the metering rod moves longitudinally relative to the barrel 1 during loading and dispensing a measured dose from the syringe barrel 1. To control the amount of the dose, arm 8 of the U-shaped base abuts a portion 6 of a handle structure on the syringe. To keep the U-shaped base member 7 from sliding on metering rod 5 as it continually bangs into a portion of the syringe handle, a clamping member 11 with a cam surface tightly grips the adjustable stop to the metering rod 5.

In FIG. 2 the adjustable stop is shown in a position traveling along with metering rod 5 as plunger 2 begins its forward, shown as downward in FIG. 2, dispensing stroke. After totally dispensing the measured dose, the plunger 2 is released and the compression coil spring retracts the plunger until the adjustable stop abuts portion 6 of the syringe handle. Because of the cam locking structure, the adjustable stop does not creep along metering rod 5 with continual usage.

In the enlarged view of FIG. 3, arm 8 of the U-shaped base member has an opening 13. The clamping member 11 has an opening 14. As a protruding handle 15 moves a camming surface 16 of clamping member 11 into contact with a floor section 10 of the base member, openings 13 and 14 are misaligned. This causes a very tight gripping force firmly positioning the stop on the metering rod 5. Metering rod 5 extends through openings 13 and 14, although such metering rod is not shown in FIG. 3 for purposes of clarity.

FIG. 4 shows the clamping member moved to a position where openings 13 and 14 are properly aligned and loosly receive the metering rod 5 (not shown in FIG. 4). Thus, when the stop is as shown in FIG. 4, the stop can be manually adjusted to the desired location on metering rod 5.

Preferably the U-shaped base has a pair of protruding ears 17 and 18 with a concave recess 19 therebetween. Recess 19 can receive a portion of the cylindrical syringe barrel and protruding ears 17 and 18 can engage the syringe barrel and limit rotational movement of the base of the stop about metering rod 5. Because the surface of recess 19 is slightly spaced from the syringe barrel, it is free to longitudinally slide along the barrel without excessive frictional contact with the barrel. By preventing rotational movement of the base relative to the metering rod 5, the syringe barrel and handle can be grasped in one hand, and protruding handle 15 in another hand for easy adjustment. There is no need to hold the U-shaped base member 7 from rotating on metering rod 5.

In the foregoing description, a specific example has been used to describe the invention. However, it is understood by those skilled in the art that modifications can be made to this example without departing from the spirit and scope of the invention.

I claim:

1. A dispensing syringe with a generally cylindrical barrel and having a dose control rod or the like with a longitudinally adjustable stop means connected thereto, wherein the improvement comprises: a pair of members with alignable openings through which the rod extends; a cam surface on one member to engage the other member to misalign the openings causing the members to grippingly engage the rod; and one member is a base with a pair of laterally spaced abutment portions for engaging the syringe barrel to limit rotational movement of the base on the rod during a dose adjustment procedure.

2. A dispensing syringe as set forth in claim 1, wherein the base is U-shaped and has arms with aligned openings receiving the rod, and a floor section joining the arms.

3. A dispensing syringe as set forth in claim 2, wherein the other member is a clamped member that has the cam surface.

4. A dispensing syringe as set forth in claim 3, wherein the cam surface of the clamped member engages the floor section of the U-shaped base.

5. A dispensing syringe as set forth in claim 3, wherein the clamped member has a protruding handle.

6. A dispensing syringe as set forth in claim 1, wherein the abutment portions include a pair of protruding ears on the base and the base has a recess between these ears for slidingly receiving a portion of the syringe barrel.

* * * * *